United States Patent [19]

Tinney

[11] 4,093,611
[45] June 6, 1978

[54] OCTAPEPTIDES AND METHODS FOR THEIR PRODUCTION

[75] Inventor: Francis John Tinney, Ann Arbor, Mich.

[73] Assignee: Parke, David & Company, Detroit, Mich.

[21] Appl. No.: 785,384

[22] Filed: Apr. 7, 1977

[51] Int. Cl.² ............................................. C07C 103/52
[52] U.S. Cl. ..................... 260/112.5 LH; 260/112.5 R
[58] Field of Search ............... 260/112.5 R, 112.5 LH

[56] References Cited

FOREIGN PATENT DOCUMENTS 2,348,221   4/1974   Germany ...................... 260/112.5 R

*Primary Examiner*—Delbert R. Phillips
*Attorney, Agent, or Firm*—Stephen Raines; David B. Ehrlinger; Frank S. Chow

[57] ABSTRACT

New octapeptides having the formula X-R-Pro-His(-benzyl)-His(benzyl)-R$^1$-Trp-D-Ala-Y wherein X is a protective group, R is Pro or Gln; R$^1$ is Tyr(benzyl)-Ser(benzyl) or Ser(benzyl)-Pro and Y is lower alkoxy, amino, lower alkylamino or di(lower alkyl)amino.

6 Claims, No Drawings

OCTAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected octapeptides that are represented by the formula

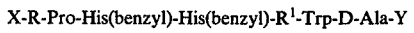
X-R-Pro-His(benzyl)-His(benzyl)-R¹-Trp-D-Ala-Y     I wherein X is a protective group, preferably t-butoxycarbonyl or benzyloxycarbonyl, R is Pro or Gln; R¹ is Tyr(benzyl)-Ser(benzyl) or Ser(benzyl)-Pro and Y is lower alkoxy, amino, lower alkylamino or di(lower alkyl)amino.

The preferred compounds of formula I are those wherein R and R¹ are as previously described, X is t-butoxycarbonyl or benzyloxycarbonyl and Y is methoxy or ethylamino.

In formula I, the conventional symbols for amino acid residues of peptide compounds linked thereto are used and each is intended to have the following meaning: Pro, D-prolyl or L-prolyl; His(benzyl), $N^{im}$-benzyl-D-histidyl or $N^{im}$-benzyl-L-histidyl; Trp, D-tryptophyl or L-tryptophyl; D-Ala, D-alanyl; Tyr(benzyl), D-tyrosyl(benzyl) or L-tyrosyl(benzyl); Ser(benzyl), D-seryl(benzyl) or L-seryl(benzyl); and Gln, D-glutaminyl or L-glutaminyl. In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. A protective group is intended to mean a group usually employed in the area of peptides for protecting an amino function, such groups are disclosed in the following texts which are incorporated by reference: E. Schroder and K. Lubke, "The Peptides", Vol. I, Chapter 1., Academic Press, 1966 and J. Meienhofer in "Hormonal Proteins and Peptides", Vol. II, p. 277., Academic Press, 1973. These symbols and terms will also be used in the formulae that follow for other compounds and each such symbol or term should be understood to have the meaning given above.

In accordance with this invention, compounds of the formula I, wherein X, R and R¹ are as previously defined and Y is lower alkoxy, are produced by removing a protected octapeptide from a resin complex of the following structure

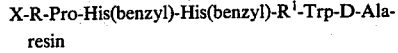
X-R-Pro-His(benzyl)-His(benzyl)-R¹-Trp-D-Ala-resin     II wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected octapeptide through a methyleneoxy bridge wherein the methylene group is attached to the polymeric portion of the resin and the oxygen atom is attached to the protected octapeptide and X, R and R¹ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein Y is amino, lower alkylamino or di(lower alkyl)amino may be prepared by reacting compounds of the formula II wherein X, R and R¹ are as previously defined, with ammonia, lower alkylamine or di(lower alkyl)amine.

The resin complex is suspended in a solvent, such as methanol, ethanol, dimethylformamide, etc., at a temperature of from about 0° C. to 50° C. for periods of from 12 hours to 10 days. When employing less reactive amines, the preferred solvent is dimethylformamide.

Certain of the complex resins of the formula II are prepared by coupling a protected amino acid of the formula

X-R-OH     III with complex resins of the formula

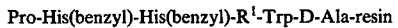
Pro-His(benzyl)-His(benzyl)-R¹-Trp-D-Ala-resin     IV wherein X, R and R¹ are as previously defined in formula I, in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about fifteen minutes to about 20 hours.

The complex resins of the formula IV are prepared by treating complex resins of the formula

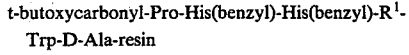
t-butoxycarbonyl-Pro-His(benzyl)-His(benzyl)-R¹-Trp-D-Ala-resin     V wherein R¹ is as previously defined in formula I with a large excess of trifluoroacetic acid utilizing dichloromethane as the solvent at temperatures of from 20° C. to 30° C. for about 10 minutes followed by neutralization of the trifluoroacetic acid salt with a base such as triethylamine.

The complex resins of the formula V are prepared by coupling

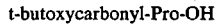
t-butoxycarbonyl-Pro-OH to complex resins of the formula

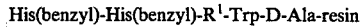
His(benzyl)-His(benzyl)-R¹-Trp-D-Ala-resin     VI wherein R¹ is as previously defined in formula I using the reaction procedure described for the preparation of compounds of the formula II.

The complex resins of the formula VI are prepared by treating the complex resins of the formula t-butoxycarbonyl-His(benzyl)-His(benzyl)-R¹-Trp-
  D-Ala-resin                                              VII wherein R¹ is as previously defined in formula I, with trifluoroacetic acid using the reaction procedure for the preparation of compounds of the formula IV.

The complex resins of the formula VII are prepared by coupling t-butoxycarbonyl-His(benzyl)-OH to complex resins of the formula His(benzyl)-R¹-Trp-D-Ala-resin                          VIII wherein R¹ is as previously defined in formula I using the reaction procedure described for the preparation of compounds of the formula II.

The complex resins of the formula VIII are prepared by treating the complex resins of the formula t-butoxycarbonyl-His(benzyl)-R¹-Trp-D-Ala-resin          IX wherein R¹ is as previously defined in formula I, with trifluoroacetic acid using the reaction procedure for the preparation of compounds of the formula IV.

The complex resins of the formula IX are prepared by coupling t-butoxycarbonyl-His(benzyl)-OH to complex resins of the formula R¹-Trp-D-Ala-resin                                       X wherein R¹ is as previously defined in formula I according to the procedure used for the preparation of compounds of formula II.

The complex resins of the formula X are prepared by treating the complex resins of the formula t-butoxycarbonyl-R¹-Trp-D-Ala-resin                      XI wherein R¹ is as previously defined in formula I with trifluoroacetic acid using the reaction procedure for the preparation of compounds of the formula IV.

The complex resins of the formula XI are prepared by coupling t-butoxycarbonyl-R²-OH to complex resins of the formula R³-Trp-D-Ala-resin                                       XII wherein R² is Ser(benzyl) or Tyr(benzyl) and R³ is Ser(benzyl) or Pro, according to the procedure used for the preparation of compounds of formula II.

The complex resins of the formula XII are prepared by treating the complex resins of the formula t-butoxycarbonyl-R³-Trp-D-Ala-resin                      XIII wherein R³ is as previously defined in formula XII with trifluoroacetic acid using the reaction procedure for the preparation of compounds of the formula IV.

The complex resins of formula XIII are prepared by coupling t-butoxycarbonyl-R³-OH to complex resins of the formula Trp-D-Ala-resin                                          XIV wherein R³ is as previously defined in formula XII according to the procedure used for the preparation of compounds of formula II.

The complex resins of the formula XIV are prepared by treating the complex resins of the formula t-butoxycarbonyl-Trp-D-Ala-resin                         XV with trifluoroacetic acid using the reaction procedure for the preparation of compounds of formula IV.

The complex resins of formula XV are prepared by coupling t-butoxycarbonyl-Trp-OH to a complex resin of the formula D-Ala-resin according to the procedure used for the preparation of compounds of formula II.

In accordance with this invention, compounds of the formula I, wherein X, R and R¹ are as previously described and Y is amino, lower alkylamino or di(lower alkyl)amino are prepared by reacting a compound of the formula I wherein Y is alkoxy, preferably methoxy, with ammonia, lower alkylamine or di(lower alkylamine).

The reactions are conducted at temperatures of from about 5° C. to 100° C. for from three hours to 4 days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein X, R and R¹ are as previously defined and Y is amino, lower alkylamino or di(lower alkyl)amino are prepared by reacting a compound of the formula X-R-Pro-His(benzyl)-His(benzyl)-R¹-Trp-D-Ala-N₃          XVI with ammonia, lower alkylamine or di(lower alkyl)amine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of the amine, about 10 percent, is preferred. When X is t-butoxycarbonyl, care should be taken to avoid the presence of a large excess of acid.

The azide compounds of the formula XVI are normally prepared in situ by reacting a peptide hydrazide of the formula X-R-Pro-His(benzyl)-His-(benzyl)-R¹-Trp-D-Ala-
     NHNH₂                                                  XVII wherein X, R and R¹ are as defined in formula I with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula XVII. The preparation of the azide is carried out at a temperature between −30° C. and 0° C. following the in situ formation of the azide of formula XVI and prior to the further reaction of the peptide azide with the appropriate amine to form certain octapeptides of formula I, a tertiary amine such as triethylamine is added to the reaction mixture to neutralize the acid used.

The compounds of formula XVII are prepared by reacting a compound of formula I wherein Y is methoxy with hydrazine hydrate in methanol.

XVIII is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Octapeptides of this invention were screened for LRF antagonist activity in vitro using rat anterior pituitary cell cultures as described by Vale et. al. [Endocrinology, 91, 562 (1972)]. The inhibition of LRF (luteinizing hormone releasing factor) induced luteinizing hormone (LH) release into the culture medium is the endpoint in this in vitro bioassay.

Following are the results of the above tests on certain preferred compounds.

| | Molar Conc. | LH Value ng/ml. | % LH Release Inhibition |
|---|---|---|---|
| ACTIVITY TABLE FOR IN VITRO TEST IN RAT ANTERIOR PITUITARY CELL CULTURES | | | |
| $N^\alpha$-Benzyloxycabonyl-L-glutaminyl-L-proplyl-$N^{im}$-benzyl-L-histidyl-$N^{im}$-benzyl-L-histidyl-O-benzyl-L-tyrosyl-O-benzyl-L-seryl-L-tryptophyl-D-alanine N-ethylamide | $1 \times 10^{-6}$ | 11.93 | 99 |
| | $3.5 \times 10^{-7}$ | 14.42 | 90 |
| | $1 \times 10^{-7}$ | 17.10 | 80 |
| | $3.5 \times 10^{-8}$ | 24.18 | 53 |
| LRF Control | $5 \times 10^{-10}$ | 38.48 | |
| Saline Control | | 11.59 | |
| $N^\alpha$Benzyloxycarbonyl-L-glutaminyl-L-propyl-$N^{im}$-benzyl-L-hisitidyl-$N^{im}$-benzyl-L-histidyl-O-benzyl-L-seryl-L-propyl-L-tryptophyl-D-alanine N-ethylamide | $1 \times 10^{-6}$ | 9.77 | 107 |
| | $3.5 \times 10^{-7}$ | 16.46 | 82 |
| | $1 \times 10^{-7}$ | 25.83 | 47 |
| | $3.5 \times 10^{-8}$ | 31.77 | 25 |
| | $1 \times 10^{-8}$ | 33.34 | 19 |
| LRF Control | $5 \times 10^{-10}$ | 38.48 | |
| Saline Control | | 11.59 | |

Compounds of the formula I wherein X, R and $R^1$ are as described in formula I and Y is amino, lower alkylamino or di(lower alkyl)amino are prepared by coupling a compound of the formula

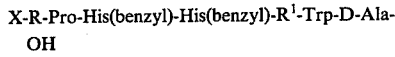

X-R-Pro-His(benzyl)-His(benzyl)-$R^1$-Trp-D-Ala-OH               XVIII with ammonia, a lower alkylamine or a di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° C. to 50° C., preferably room temperature for periods of from ten hours to five days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula XVIII are prepared by the hydrolysis of a compound of formula I wherein X, R and $R^1$ are as previously defined and Y is lower alkoxy. The reaction is conducted at temperatures of from 20° C. to 30° C. using about 0.5 ml. of two normal aqueous sodium hydroxide solution and 10 ml. of solvent, usually water or an alcohol such as methanol, for each millimole of ester. The compound of formula The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the octapeptides of this invention are useful in controlling ovulation and in restricting fertility.

The invention is illustrated by the following examples.

EXAMPLE 1

The ethanol and ether washed $N^\alpha$-benzyloxycarbonyl-L-glutaminyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine resin, 15 g., is stirred in 200 ml. of methanol and 20 ml. of triethylamine at room temperature for 2 days. After filtration and evaporation, the crude product is chromatographed on silica gel with 5% methanol in benzene giving 1.4 g. of $N^\alpha$-benzyloxycarbonyl-L-glutaminyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine methyl ester as a monohydrate; m.p. 95°–100° C.; $[\alpha]_D^{23}$ −25.6° (c 1, methanol).

$N^\alpha$-Benzyloxycarbonyl-L-glutaminyl-L-prolyl-$N^{im}$-benzyl-L-histidyl-$N^{im}$-benzyl-L-histidyl-O-benzyl-L-tyrosyl-O-benzyl-L-seryll-tryptophyl-D-alanine resin is prepared by the General Procedure, given below, by successive coupling of 30 g. (0.0198 mol) of $N^\alpha$-t-butoxycarbonyl-D-alanine resin with 1.) 9.1 g (0.03 mol) of $N^\alpha$-t-butoxycarbonyl-L-tryptophan and 6.8 g. (0.03 mol) of dicyclohexylcarbodiimide, 2.) 9.0 g. (0.03 mol) of $N^\alpha$-t-butoxycarbonyl-O-benzyl-L-serine and 6.8 g. (0.033 mol) of dicyclohexylcarbodiimide, 3.) 11.1 g. (0.03 mol) of $N^\alpha$-t-butoxycarbonyl-O-benzyl-L-tyrosine and 6.8 g. (0.033 mol) of dicyclohexylcarbodiimide, 4.) 10.5 g. (0.03 mol) of $N^\alpha$-t-butoxycarbonyl-$N^{im}$-benzyl-L-histidine and 6.8 g. (0.033 mol) of dicyclohexylcarbodiimide, 5.) 10.5 g. (0.03 mol) of $N^\alpha$-t-butoxycarbonyl-$N^{im}$-benzyl-L-histidine and 6.8 g. (0.033 mol) of dicyclohexylcarbodiimide, 6.) using ⅔ of the resin obtained in Step 5 with 4.4 g. (0.02 mol) of $N^\alpha$-t-butoxycarbonyl-L-proline and 4.6 g. (0.022 mol) of dicyclohexylcarbodiimide and 7.) using ½ of the resin obtained in Step 6 with 8 g. (0.02 mol) of $N^\alpha$-benzyloxycarbonyl-L-glutamine p-nitrophenyl ester in dimethylformamide solution and the excess removed by drainage.

General Procedure for the Solid Phase Synthesis of Peptide Resins

The peptide resin is obtained by attaching an α-amino-protected amino acid to a resin (usually a chloromethylated resin which is commercially available from Lab Systems, Inc., San Mateo, California). The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart "Solid Phase Peptide Synthesis", W. H. Freeman and Co., 1969.

Each cycle of the procedure follows the scheme:
1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. 15 to 30 minutes agitation with the α-amino-protected amino acid which is present in up to a fourfold molar excess based on the resin nitrogen analysis. However when a large excess of the α-amino-protected amino acid is used it is agitated with the resin for fifteen minutes and the excess recovered by draining the solution from the reactor.
6. Addition of dicyclohexylcarbodiimide at least equivalent to the α-amino-protected amino acid in Step 5 in dichloromethane followed by agitation for four to twenty hours. In the alternate method, a 3.3-fold excess of dicyclohexylcarbodiimide is used relative to the α-amino-protected amino acid resin.
7. Three washes with dichloromethane.

$N^\alpha$-t-Butoxycarbonyl-D-alanine resin is prepared by mixing 110 g. of 1% chloromethylated resin, 27 g. (0.143 mol) $N^\alpha$-t-butoxycarbonyl-D-alanine and 14.5 g. (0.143 mol) of triethylamine in 600 ml. of ethanol. The mixture is refluxed overnight, filtered, the resin washed with ethanol, water, methanol and ether and dried; 111 g. Analysis for nitrogen shows 0.00066 mol per gram.

EXAMPLE 2

The methyl ester of Example 1, 400 mg. (0.00026 mol), is added to a mixture containing 5 ml. of ethylamine, 10 ml. of dimethylformamide and 140 ml. of methanol and let stand at room temperature for 4 days. The product, $N^\alpha$-benzyloxycarbonyl-L-glutaminyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine N-ethylamide monohydrate is obtained by precipitation from dimethylformamide solution with anhydrous ether; 270 mg.; m.p. 102°–107° C.; $[\alpha]_D^{23}$ −22.7° (c 1.03, methanol).

EXAMPLE 3

$N^\alpha$-Benzyloxycarbonyl-L-prolyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine resin, 15.3 g., is stirred with 20 ml. of triethylamine and 200 ml. of methanol at room temperature for 2 days. After filtration and evaporation, the crude product is chromatographed on silica gel with 20% methanol in chloroform and then with 5% methanol in benzene yielding 500 mg. of $N^\alpha$-benzyloxycarbonyl-L-prolyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine methyl ester; m.p. 95°–100° C.; $[\alpha]_D^{23}$ −33° (c 1.04, methanol).

$N^\alpha$-Benzyloxycarbonyl-L-prolyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine resin is obtained according to the General Procedure of Example 1 except that 2.5 g. (0.01 mol) of $N^\alpha$-benzyloxycarbonyl-L-proline and 2.3 g. (0.011 mol) of dicyclohexylcarbodiimide are used in place of the $N^\alpha$-benzyloxycarbonyl-L-glutamine p-nitrophenyl ester and dimethylformamide.

EXAMPLE 4

The methyl ester from Example 3, 0.3 g., 0.0002 mol, is reacted with 5 ml. of ethylamine in a mixture of 10 ml. of dimethylformamide and 140 ml. of methanol for 4 days. The product, $N^\alpha$-benzyloxycarbonyl-L-prolyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine N-ethylamide, 0.15 g., is obtained as a hydrate after evaporation of the solvent and recrystallization of the residue from dimethylformamide and ether; m.p. 100°–105° C.

EXAMPLE 5

$N^\alpha$-Benzyloxycarbonyl-L-glutaminyl-L-prolyl-$N^{im}$-benzyl-L-histidyl-$N^{im}$-benzyl-L-histidyl-O-benzyl-L-seryl-L-prolyl-L-tryptophyl-D-alanine resin, 13.8 g., is mixed with 200 ml. of methanol and 20 ml. of triethylamine at room temperature for 2 days. After filtration and evaporation, the crude product, an oil, is purified by chromatography on silica gel with 5% methanol in benzene giving 1.04 g. of $N^\alpha$-benzyloxycarbonyl-L-glutaminyl-L-prolyl-$N^{im}$-benzyl-L-histidyl-$N^{im}$-benzyl-L-histidyl-O-benzyl-L-seryl-L-prolyl-L-tryptophyl-D-alanine methyl ester; m.p. 98°–103 C.; $[\alpha]_D^{23}$ −46° (c 1.06, DMF).

$N^\alpha$-Benzyloxycarbonyl-L-glutaminyl-L-prolyl-$N^{im}$-benzyl-L-histidyl-$N^{im}$-benzyl-L-histidyl-O-benzyl-L-seryl-L-prolyl-L-tryptophyl-D-alanine resin is obtained according to the General Procedure of Example 1, by successive coupling of 40 g. (0.0264 mol) of $N^\alpha$-t-butoxycarbonyl-D-analine resin with 1.) 12.2 g. (0.04 mol) of $N^\alpha$-t-butoxycarbonyl-L-tryptophan and 9.2 g. (0.045 mol) of dicyclohexylcarbodiimide, 2.) using ¼ of the resin obtained in step 1 with 2.2 g. (0.01 mol) of $N^\alpha$-t-butoxycarbonyl-L-proline and 2.3 g. (0.01 mol) of dicyclohexylcarbodiimide, 3.) 3.0 g. (0.01 mol) of $N^\alpha$-t-butoxycarbonyl-O-benzyl-L-serine and 2.3 g. of dicyclohexylcarbodiimide, 4.) 3.5 g. (0.01 mol) of $N^\alpha$-t-butoxycarbonyl-$N^{im}$-benzyl-L-histidine and 2.3 g. of dicyclohexylcarbodiimide, 5.) 3.5 g. of $N^\alpha$-t-butoxycarbonyl-$N^{im}$-benzyl-L-histidine and 2.3 g. of dicyclohexylcarbodiimide, 6.) 2.2 g. (0.01 mol) of $N^\alpha$-t-butoxycarbonyl-L-proline and 2.3 g. of dicyclohexylcarbodiimide and 7.) 8 g. (0.02 mol) of $N^\alpha$-benzyloxycarbonyl-L-glutamine p-nitrophenyl ester in dimethylformamide solution.

EXAMPLE 6

The methyl ester of Example 5, 400 mg. (0.00029 mol), is stirred with 5 ml. of ethylamine, 10 ml. of dimethylformamide and 140 ml. of methanol at room temperature for 3 days. The methanol is removed under reduced pressure and the product precipitated by the addition of 300 ml. of anhydrous ether yielding 280 mg. of $N^\alpha$-benzyloxycarbonyl-L-glutaminyl-L-prolyl-$N^{im}$-benzyl-L-histidyl-$N^{im}$-benzyl-L-histidyl-O-benzyl-L-seryl-L-prolyl-L-tryptophyl-D-alanine N-ethylamide sesquihydrate; m.p. 110°–115° C.; $[\alpha]_D^{25}$ −50° (c 0.79, methanol).

I claim:

1. An octapeptide having the name $N^\alpha$-benzyloxycarbonyl-L-glutaminyl-L-prolyl-$N^{im}$-benzyl-L-histidyl-$N^{im}$-benzyl-L-histidyl-O-benzyl-L-seryl-L-prolyl-L-tryptophyl-D-alanine N-ethylamide.

2. An octapeptide having the name $N^\alpha$-benzyloxycarbonyl-L-glutaminyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine N-ethylamide.

3. A compound having the name $N^\alpha$-benzyloxycarbonyl-L-glutaminyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine methyl ester.

4. A compound having the name $N^\alpha$-benzyloxycarbonyl-L-prolyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine methyl ester.

5. A compound having the name $N^\alpha$-benzyloxycarbonyl-L-prolyl-L-prolyl-$N^{im}$-benzyl-L-histidyl-$N^{im}$-benzyl-L-histidyl-O-benzyl-L-tyrosyl-O-benzyl-L-seryl-L-tryptophyl-D-alanine methyl ester.

6. A compound having the name $N^\alpha$-benzyloxycarbonyl-L-glutaminyl-L-prolyl-$N^{im}$-benzyl-L-histidyl-$N^{im}$-benzyl-L-histidyl-O-benzyl-L-seryl-L-prolyl-L-tryptophyl-D-alanine methyl ester.

* * * * *